US008919343B2

(12) United States Patent
Radomski et al.

(10) Patent No.: US 8,919,343 B2
(45) Date of Patent: Dec. 30, 2014

(54) RESPIRATOR WITH ACTIVE DEHUMIDIFICATION

(75) Inventors: Klaus Radomski, Luebeck (DE); Henning Gerder, Luebeck (DE)

(73) Assignee: Dräger Medical AG & Co. KG, Lübeck (DE)

(*) Notice: Subject to any disclaimer, the term of this patent is extended or adjusted under 35 U.S.C. 154(b) by 2249 days.

(21) Appl. No.: 11/551,885

(22) Filed: Oct. 23, 2006

(65) Prior Publication Data

US 2007/0157929 A1 Jul. 12, 2007

(30) Foreign Application Priority Data

Dec. 23, 2005 (DE) .......................... 10 2005 062 185

(51) Int. Cl.
| A61M 16/00 | (2006.01) |
| A62B 7/00 | (2006.01) |
| A61M 16/10 | (2006.01) |
| A61M 16/16 | (2006.01) |
| A61M 16/01 | (2006.01) |
| A61M 16/08 | (2006.01) |

(52) U.S. Cl.
CPC ... A61M 16/1075 (2013.01); *A61M 2205/3673* (2013.01); A61M 16/1095 (2014.02); *A61M 16/16* (2013.01); *A61M 2205/3368* (2013.01); *A61M 16/01* (2013.01); *A61M 16/0808* (2013.01); *A61M 16/0066* (2013.01)

USPC ............. 128/204.18; 128/204.15; 128/204.17

(58) Field of Classification Search
CPC . A61M 16/16; A61M 16/1075; A61M 16/08; A61M 16/1045
USPC ............. 128/204.18, 204.15, 203.17, 203.16, 128/203.26, 203.27, 204.14, 204.17
See application file for complete search history.

(56) References Cited

U.S. PATENT DOCUMENTS

| 5,482,031 A * | 1/1996 | Lambert ................... 128/203.12 |
| 6,131,571 A * | 10/2000 | Lampotang et al. ...... 128/204.21 |
| 6,523,538 B1* | 2/2003 | Wikefeldt ................ 128/204.18 |
| 7,438,072 B2* | 10/2008 | Izuchukwu .............. 128/203.15 |
| 2004/0149284 A1* | 8/2004 | Smith et al. .............. 128/203.16 |
| 2004/0210153 A1* | 10/2004 | Tsukashima et al. .......... 600/532 |
| 2006/0037613 A1* | 2/2006 | Kwok et al. ............. 128/203.27 |

FOREIGN PATENT DOCUMENTS

| EP | 0533644 A2 | 3/1993 |
| WO | WO 01 49351 A2 | 7/2001 |
| WO | WO 2004 082729 A2 | 9/2004 |

* cited by examiner

Primary Examiner — Jusinte Yu
Assistant Examiner — Colin W Stuart
(74) Attorney, Agent, or Firm — McGlew and Tuttle, P.C.

(57) ABSTRACT

A respirator with active dehumidification of the breathing gas has a breathing gas cooler in the form of a Peltier element (16), whose warm side is arranged in the inspiration line 7 and whose cold side (18) is arranged in the expiration line 12.

18 Claims, 8 Drawing Sheets

RESPIRATOR WITH ACTIVE DEHUMIDIFICATION

CROSS REFERENCE TO RELATED APPLICATIONS

This application claims the benefit of priority under 35 U.S.C. §119 of German Patent Application DE 10 2005 062 18 5.6 filed Dec. 23, 2005, the entire contents of which are incorporated herein by reference.

FIELD OF THE INVENTION

The present invention pertains to a respirator (also known as a ventilator) with an inspiration branch and an expiration branch.

BACKGROUND OF THE INVENTION

There are various different possibilities of heating and humidifying breathing air. The goal is to supply the patient with humid and preheated air. The problem in breathing gas humidification is to adjust the humidity supplied to the velocity of flow and to the gas flow. This adjustment is necessary to avoid overheating of the breathing gas, on the one hand, and to extensively prevent the formation of water of condensation, on the other hand. Breathing gas humidifiers in which water is heated in a water reservoir and is fed into the flowing breathing gas in the form of water vapor are known.

Water traps or also desiccants, which collect the water of condensation passively at the device, are used for dehumidification and for removing water of condensation. However, it cannot be avoided that the formation of water of condensation will nevertheless take place within the respiration system. Heating foils, with which the respiration system can be heated over a large surface, are known for reducing the formation of water of condensation within the respiration system. The problem is additionally aggravated in the case of a closed breathing circuit in anesthesia by the fact that moisture, which must be removed from the system, is formed additionally due to the absorption of carbon dioxide in the carbon dioxide adsorber. Filter systems, which initially heat the inspired gas in the form of a heat exchanger and extract moisture from the expired gas, are known for reducing the moisture in the breathing gas. The moisture of the breathing gas, which moisture is being stored in the filter, is again introduced into the inspired gas during the next inspiration stroke. Such a filter is known from EP 533 644 A2. The drawback of the prior-art filter is that only a limited quantity of moisture can be stored.

SUMMARY OF THE INVENTION

The basic object of the present invention is to provide a respirator in which the moisture in the breathing gas is maintained within limits favorable for the patient without water of condensation being formed in an uncontrolled manner.

According to the invention, a breathing gas cooler is provided, which cools the breathing gas in the expiration branch by a few degrees in order to lower the dew point at this site in a controlled manner and to bring about the formation of water of condensation. The condensed water can be collected there and can be removed from the respiration circuit, for example, by means of a water trap.

A Peltier element is advantageously used as the breathing gas cooler. The expiratory breathing gas is now cooled actively by means of the cold side of the Peltier element, while the warm side of the Peltier element is arranged in the inspiration branch and heats the inspired gas.

Provisions are made in an alternative embodiment of the present invention for arranging in the expiration branch an additional Peltier element, whose cold side is exposed to the expiration flow, while the warm side is cooled by a speed-controlled fan. The speed control of the fan and the supply of power to the additional Peltier element can now be derived from the breathing pattern of the respirator, or it is varied manually by the user such that the desired degree of dehumidification is reached. It is expedient now to arrange the warm side of the additional Peltier element in a channel through which cooling air flows.

Various possibilities are conceivable for varying the electric power of the Peltier element. For example, the electric power supplied to the Peltier element can be kept low during the start phase of anesthesia with, for example, because the breathing gas flow is still relatively dry at that time. Slight cooling of the expired gas flow is sufficient in this case to eliminate the moisture. It is especially advantageous to control the supply of electric power to the Peltier element in proportion to the breathing gas flow during the phase of operation. As a result, especially effective dehumidification of the expired gas can be achieved.

As an alternative to the propoportional control of power supply to the Peltier element, it is also possible to set an average power manually, which is suitable for the stationary operation, at the final control element. The setting of the power can be adapted individually by the user during the phase of introduction and the final phase of anesthesia. The breathing gas sensor is expediently connected directly to a flexible breathing tube system. However, it is also possible to integrate the breathing gas sensor in a respiration system, so that the user has no additional components outside the respiration system.

Exemplary embodiments of the present invention are shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiment of the invention is illustrated.

DESCRIPTION OF THE PREFERRED EMBODIMENTS

Figure 1:
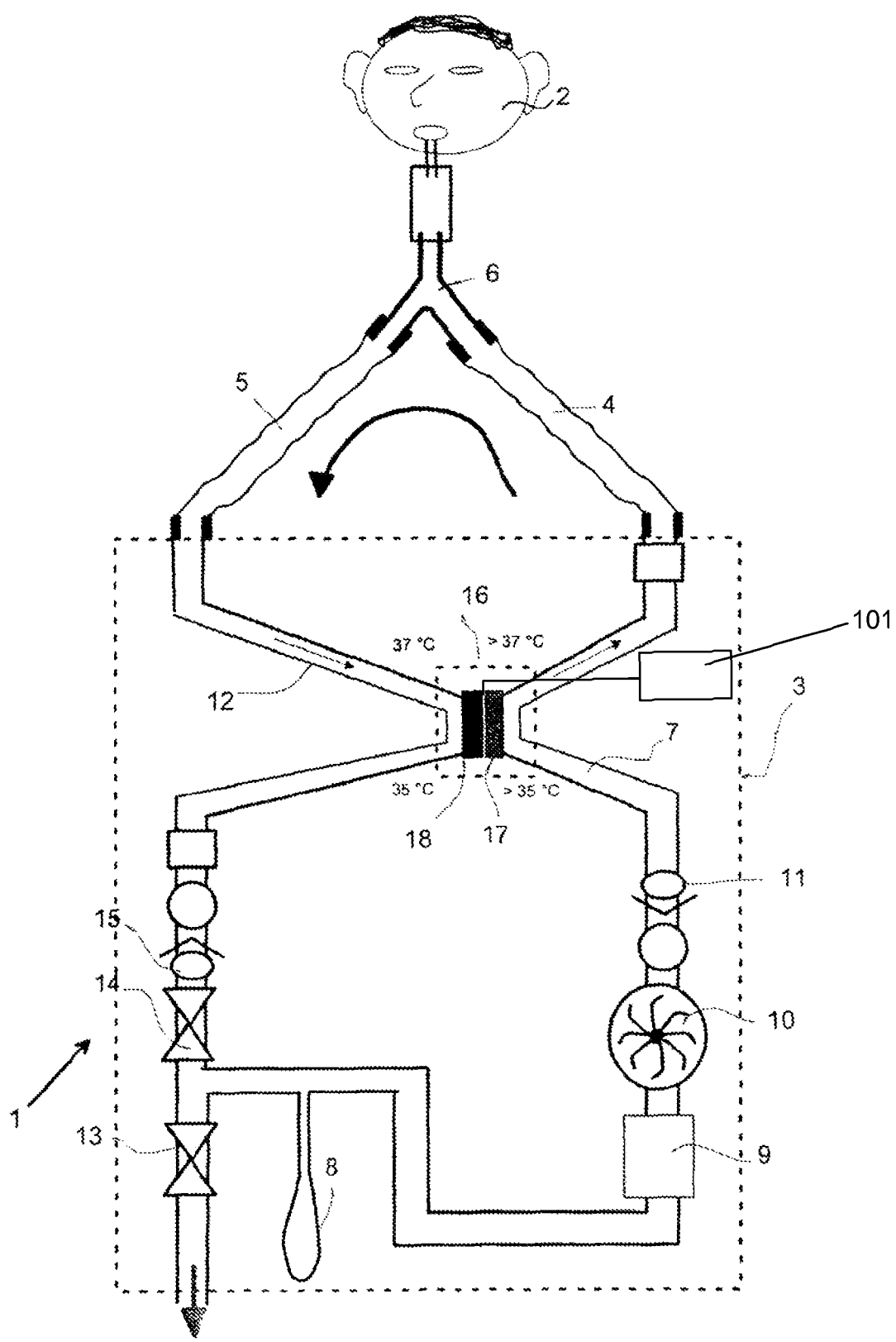
FIG. 1 is a schematic view of a closed breathing gas system with a Peltier element as a breathing gas cooler according to the invention.

Referring to the drawings in particular, FIG. 1 schematically illustrates a respirator 1 for a patient 2, in which a breathing system 3 with breathing air circulation via a flexible inspiration tube 4, a flexible expiration tube 5 and a Y-piece 6 is connected to the patient 2.

A breathing bellows 8, a carbon dioxide absorber 9, a fan 10, an inspiration valve 11 and an expiration line 12 connected to the inspiration line 7, an excess gas outlet valve 13, a peep valve 14 and an expiration valve 15 are located in an inspiration line 7 of the respiration system 3. The inspiration line 7 and the expiration line 12 are thermally coupled with one another via a Peltier element 16. The warm side 17 of the Peltier element 16 is arranged in the inspiration line 7 and the cold side 18 in the expiration line 12. The breathing gas in the inspiration line 7, which gas is being delivered by the fan 10 with a temperature of about 35° C., is heated by the Peltier element 16 to a value somewhat above 37° C. The gas breathed out by the patient 2 is cooled in the expiration line 12 to about 35° C. by the cold side 18 of the Peltier element 16, as a result of which moisture condenses and can be removed via a water trap, which is not shown in more detail. A power supply 101 supplies power to the Peltier element 16.

The Peltier element 16 has a power consumption of about 5 W, the cold side 18 has a surface area of about 100 cm$^2$ and the surface area of the warm side 17 is somewhat larger than this value.

Figure 2:
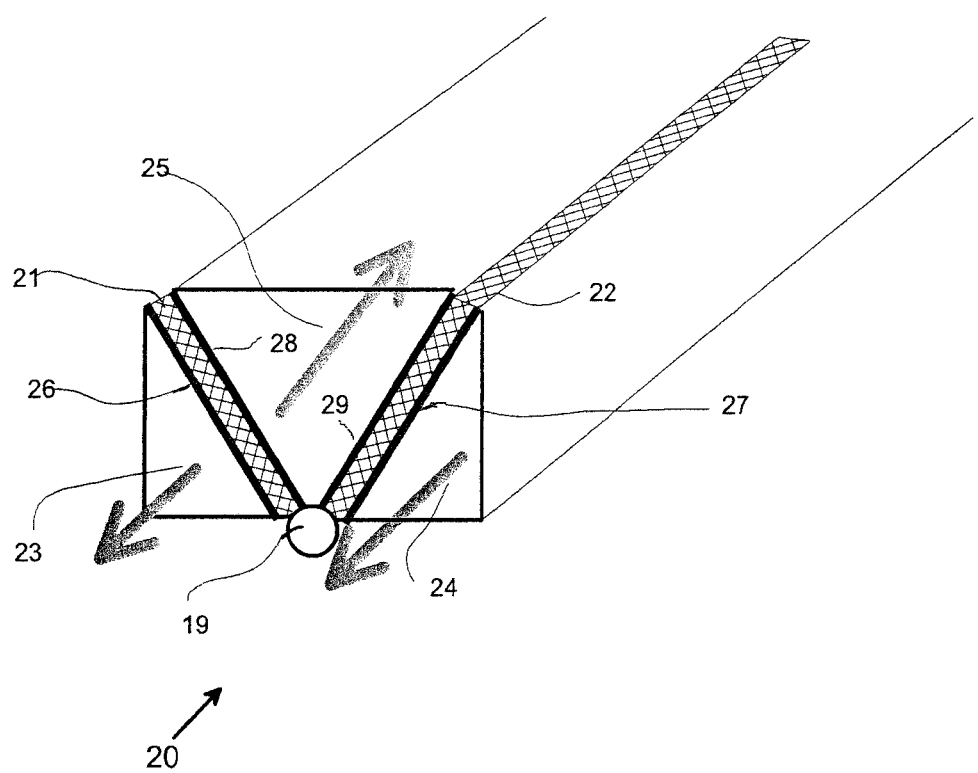
FIG. 2 is a schematic view showing an alternative embodiment with two Peltier elements arranged in a V-shaped pattern in relation to one another.

In a first alternative embodiment 20 of a Peltier sensor corresponding to FIG. 2, two inspiration channel sections 23, 24 and an expiration channel 25 are limited by Peltier elements 21, 22 arranged in a V-shaped pattern. The warm sides 26, 27 of the Peltier elements 21, 22 are arranged in the inspiration channel sections 23, 24 each, while the cold sides 28, 29 of the Peltier elements 21, 22 define the expiration channel 25. Condensed water is drawn off via a water of condensation collection line 19.

Figure 3:
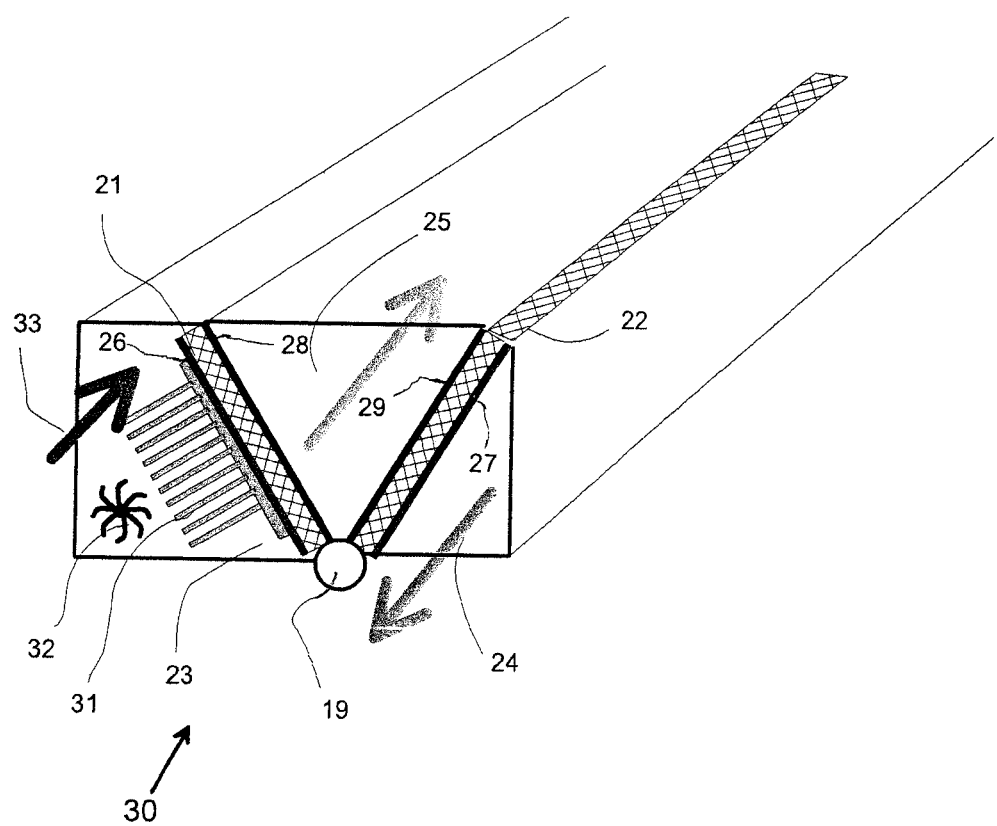
FIG. 3 is a schematic view showing an alternative embodiment of a breathing gas cooler for FIG. 2 with a channel through which cooling air flows.

A second alternative embodiment 30 shown in FIG. 3 differs from the first alternative embodiment 20 according to FIG. 2 in that the left-hand inspiration channel section 23 is designed as a channel through which cooling air flows and in which the warm side 26 of the left Peltier element 21 is provided with cooling ribs 31. A fan 32 delivers cooling air through the channel 23 in the direction of arrow 33. Higher cooling output of the left-hand Peltier element 21 in the expiration channel section 25 is thus attained.

Figure 4:
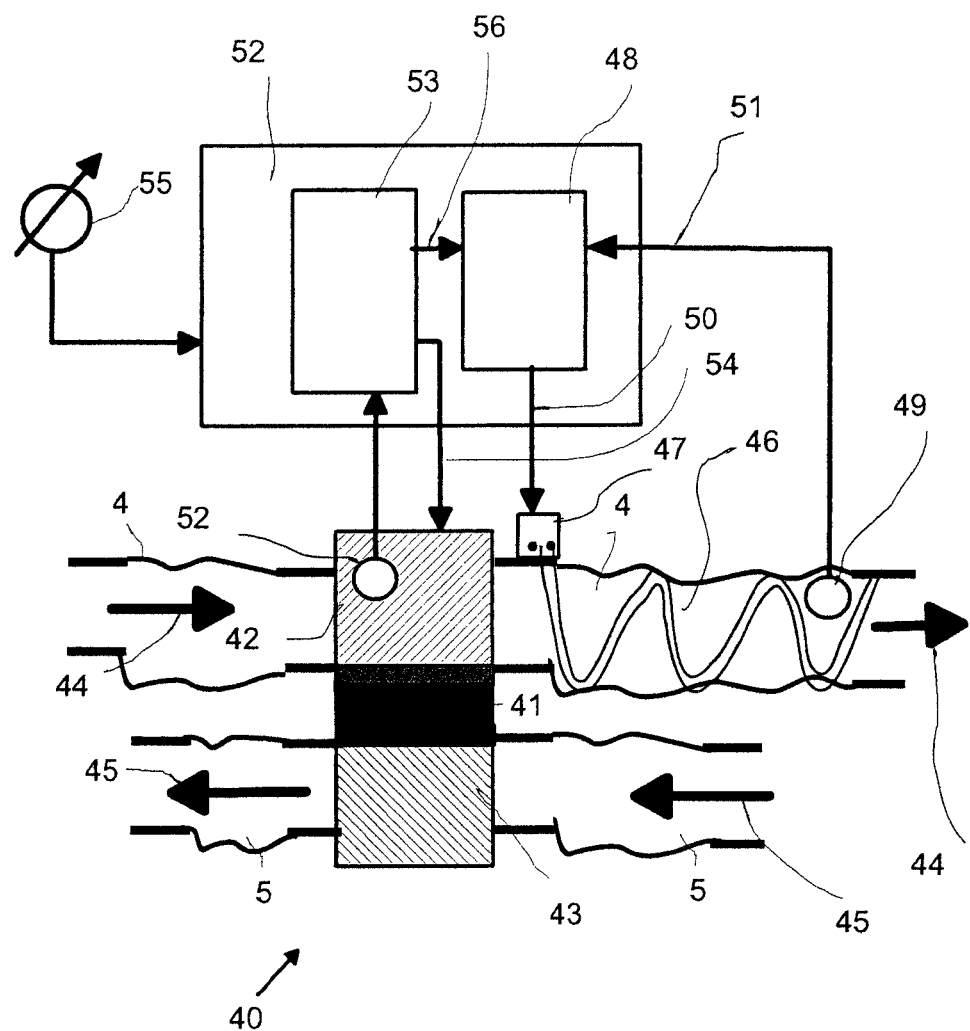
FIG. 4 is a schematic view showing a first cooling device with a breathing gas-heating unit for the Peltier element.

FIG. 4 schematically illustrates the design of a first cooling device 40, in which the warm side 42 of a Peltier element 41 is arranged in the flexible inspiration tube 4 and the cold side 43 in the flexible expiration tube 5. The direction of flow of the breathing gas is indicated by arrows 44, 45. The flexible inspiration tube 4 is provided with a heating coil 46 as a tube heater, which is connected to a breathing gas temperature-regulating unit 48 via a plug-in coupling 47. A breathing gas temperature sensor 49 detects the breathing gas temperature at the end of the heating coil 46. The heating coil 46 is supplied with electricity via a connection cable 50 extending from the breathing gas temperature-regulating unit 48 to the plug-in coupling 47. The actual value of the breathing gas temperature detected by the temperature sensor 49 reaches the breathing gas temperature-regulating unit 48 via a signal line 51.

A first Peltier temperature sensor 52 detects the actual value of the temperature of the warm side 42 of the Peltier element 41. A first Peltier control unit 53, which receives the measured value of the temperature sensor 52, supplies the electricity for the Peltier element 41 via a supply line 54. Via an adjusting element 55 for the heating and cooling power of the Peltier element 41, the Peltier control unit 52 receives a preset value for the electricity to be supplied to the Peltier element 41. The temperature sensor 52 detects the actual value of the temperature of the warm side 42 of the Peltier element 41 and the first Peltier control unit 52 calculates from this a preset set point 56 for the breathing gas temperature-regulating unit 48 in order to reach a breathing gas temperature between 37° C. and 38° C. at the end of the heating coil 46. The first Peltier control unit 53 and the breathing gas temperature-regulating unit 48 together form a first breathing gas heating unit 57.

Figure 5:
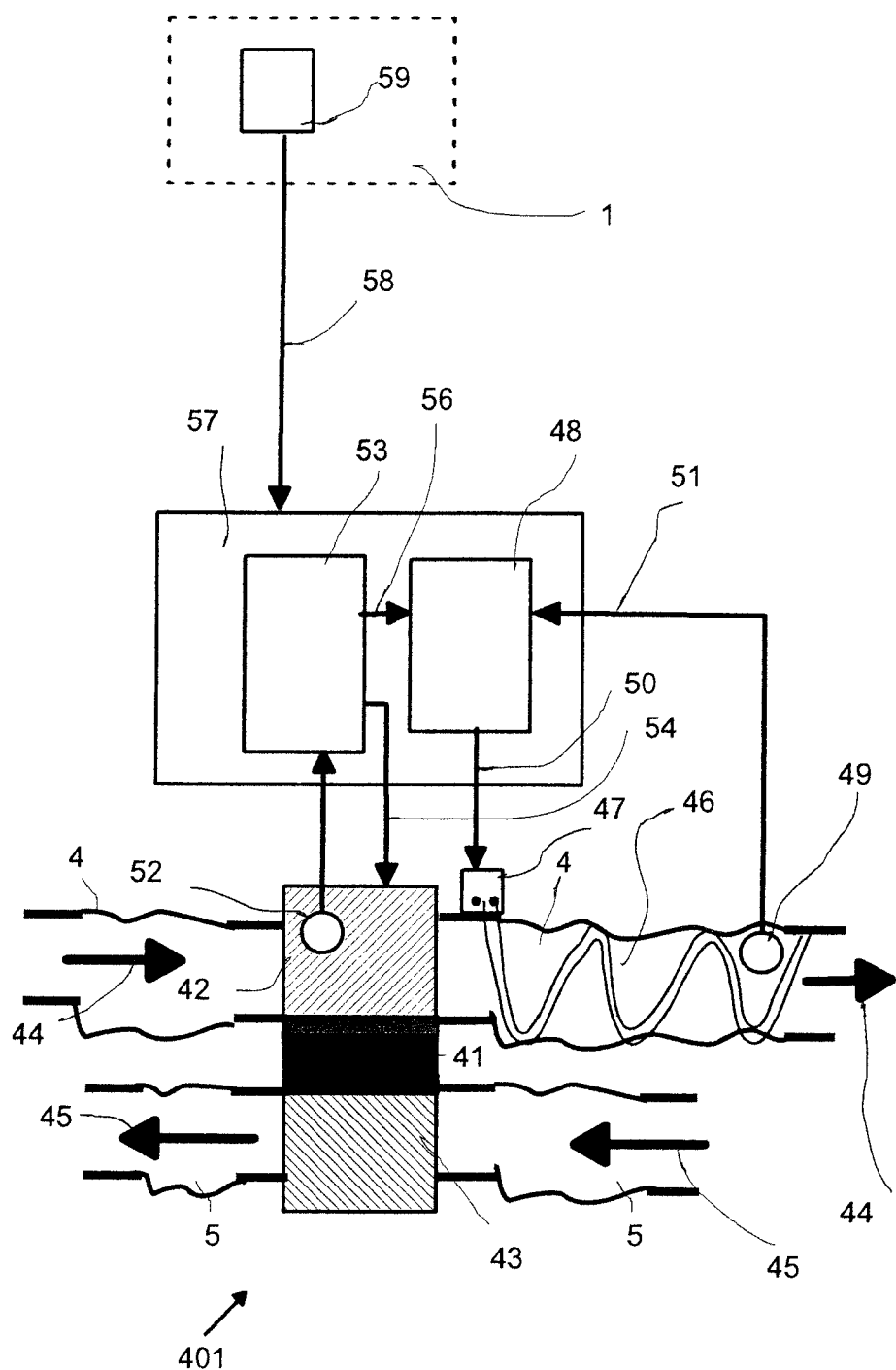
FIG. 5 is a schematic view showing an alternative embodiment of the first cooling device according to FIG. 4 with power control from a respirator.

The adjusting element 55 is designed as a potentiometer or keypad that can be operated by the user. The adjusting element may also be designed, corresponding to FIG. 5, in the form of a bidirectional data line 58, which is connected to the respirator 1 and receives corresponding preset values for actuating the Peltier element 41 from this. The data line 58 is connected for this purpose to a control unit 59 of the respirator 1, FIG. 1.

Figure 6:
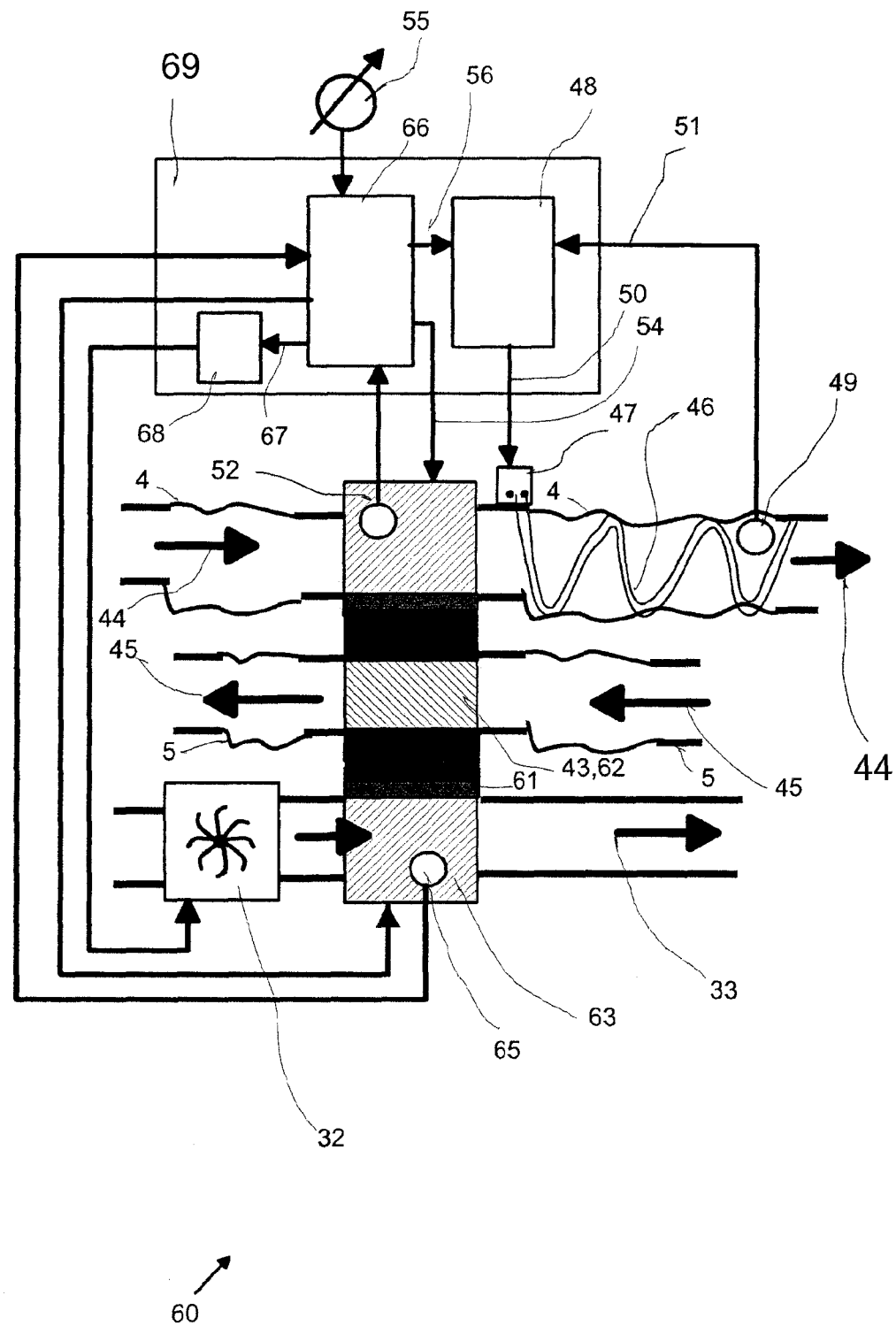
FIG. 6 is a schematic view showing a second cooling device with an additional Peltier element.

A second cooling device 60 shown in FIG. 6 contains, compared to the first cooling device 40 according to FIG. 4, an additional Peltier element 61, whose cold side 62 is arranged in the flexible expiration tube 5 and whose warm side 63 is arranged in the flow channel 64 with the fan 32. The cold sides 43, 62 of the Peltier elements 41, 61 together cool the breathing gas in the flexible expiration tube 5. There is a greater reduction in temperature in the flexible expiration tube 5 due to the additional Peltier element 61. A second Peltier temperature sensor 65, which detects the temperature of the warm side 63 of the Peltier element 61, is connected to a second Peltier control unit 66, which supplies a preset value 67 for a speed controller 68 controlling the fan 32.

The second Peltier control unit 66 and the breathing gas temperature-regulating unit 48 together form a second breathing gas heating unit 69. Identical components are designated by the same reference numbers as in FIGS. 3 and 4.

Figure 7:
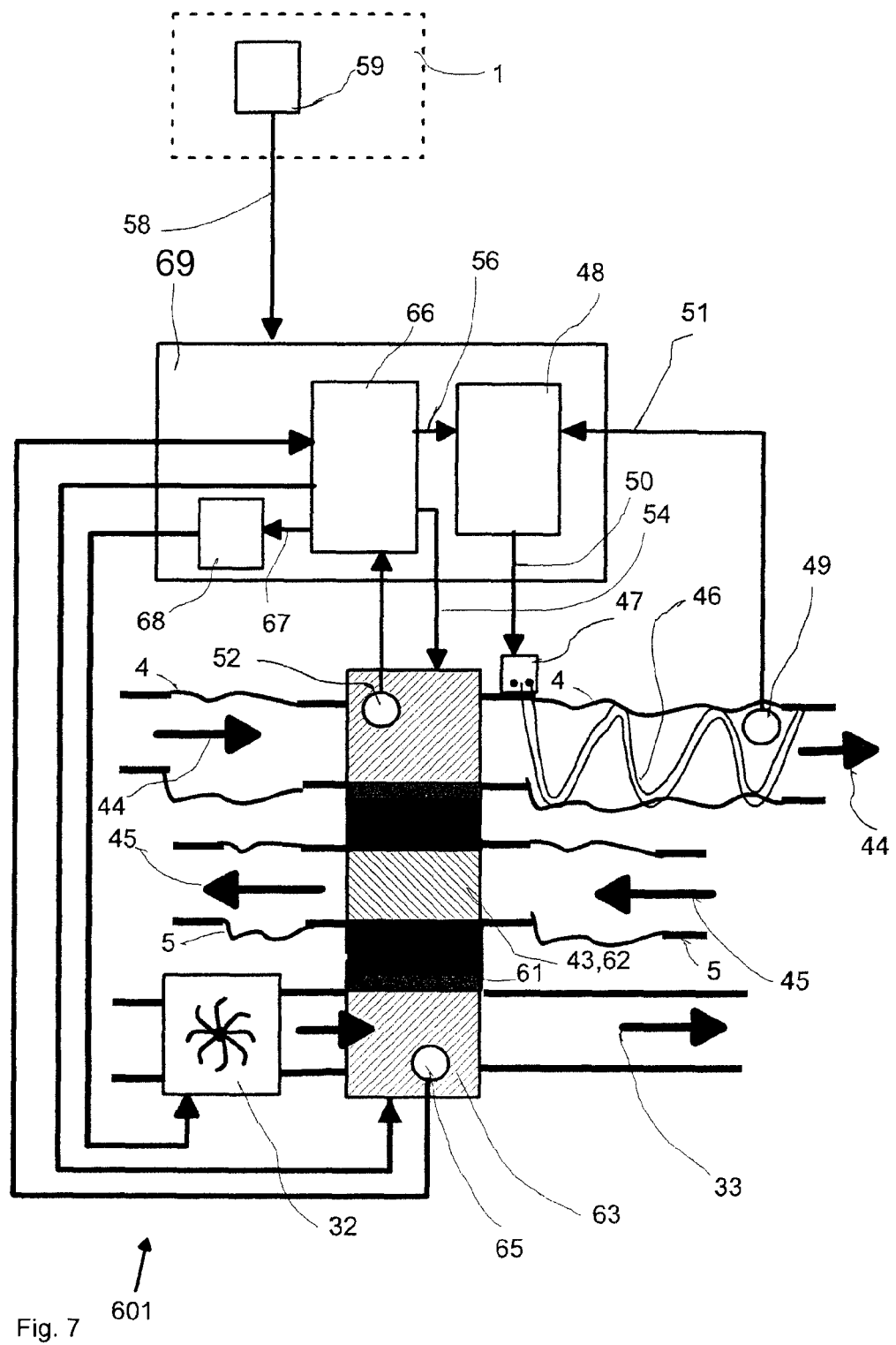
FIG. 7 is a schematic view showing the cooling device according to FIG. 6 with control from a respirator.

The alternative second cooling device 601 shown in FIG. 7 differs from the second cooling device 60 according to FIG. 6 by the bidirectional data line 58 connected to the control unit 59 of the respirator 1. Via the data line 58, the second Peltier control unit 66 receives preset values for controlling the Peltier elements 41, 61.

Figure 8:
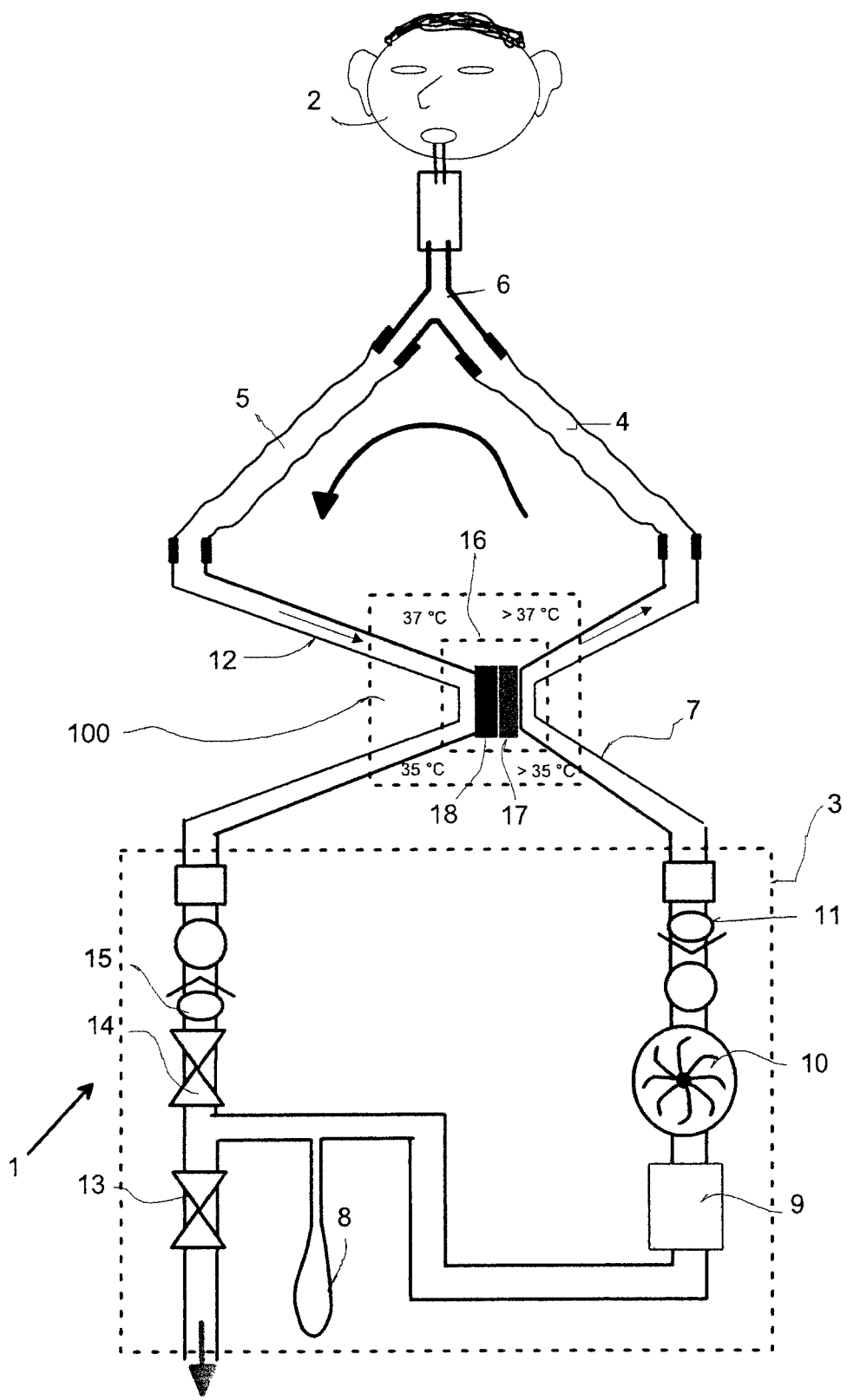
FIG. 8 is an alternative embodiment for FIG. 1 with a breathing gas cooler separated from the closed breathing gas system.

FIG. 8 shows an alternative cooling device for FIG. 1, in which a breathing gas cooler 100 with the Peltier element 16 is arranged separately from the respiration system 3. The breathing gas cooler 100 is designed as a component that can be coupled with the flexible breathing tube system (4, 5).

While specific embodiments of the invention have been shown and described in detail to illustrate the application of the principles of the invention, it will be understood that the invention may be embodied otherwise without departing from such principles.

What is claimed is:
1. A respirator comprising:
   an inspiration branch;
   an expiration branch receiving an expired fluid flow;
   a breathing gas cooler for cooling gas in said expiration branch, at least a portion of said breathing gas cooler being exposed to only said expired fluid flow in said expiration branch; and a control means for controlling activation of said breathing gas cooler such that an amount of condensation formed in said expiration branch is controlled via said control means, said breathing gas cooler comprising a Peltier element having a warm side and a cold side, said inspiration branch receiving an inspired fluid flow, said warm side being exposed only to said inspired fluid flow in said inspiration branch, said cold side being exposed to only said expired fluid flow, wherein said warm side is not in direct fluid communication with said expired fluid flow, and said cold side is not in direct fluid communication with said inspired fluid flow.

2. A respirator in accordance with claim 1, wherein said warm side of said Peltier element is positioned in contact with gas in said inspiration branch, said inspiration branch comprising an inspiration line, said expiration branch comprising an expiration line, said warm side being arranged in said inspiration line, said warm side being in contact with the inspired fluid flow in said inspiration line such that said inspired fluid flow is heated via said warm side, said cold side being arranged in said expiration line, said cold side being in contact with said expired fluid flow in said expiration line such that said expired fluid flow is cooled via said cold side, wherein said cold side removes heat from said expired fluid flow such that condensation of water forms, wherein said control means controls power supplied to said Peltier element to control a transfer of heat from said cold side to said warm side, whereby a temperature of said cold side and a temperature of said warm side are controlled via said control means.

3. A respirator in accordance with claim 2, wherein said expiration branch has an additional Peltier element with a warm side and a cold side as an additional breathing gas cooler, said cold side of said additional Peltier element being exposed to at least one expired fluid flow in said expiration branch.

4. A respirator in accordance with claim 3, wherein said warm side of said additional Peltier element is arranged in a channel, through which cooling air flows.

5. A respirator in accordance with claim 2, wherein said breathing gas cooler is part of a respiration system that can be coupled with respirator components.

6. A respirator in accordance with claim 2, wherein said inspiration branch and said expiration branch comprise a flexible breathing tube system and said breathing gas cooler is a component that can be coupled with said flexible breathing tube system.

7. A respirator in accordance with claim 2, further comprising:
a power supply for supplying power to said Peltier element in a breathing flow-controlled manner.

8. A respirator in accordance with claim 2, wherein said Peltier element receives control data from said control means.

9. A respirator comprising:
a breathing tube system with an inspiration branch and an expiration branch, said inspiration branch receiving an inspired gas flow, said expiration branch receiving an expired gas flow;
a means for supplying breathing gas to the inspiration branch;
a breathing gas cooler for cooling gas in said expiration branch, wherein said breathing gas cooler cools said expired gas flow such that moisture in said expired gas flow condenses to form water condensation; and
a control device controlling activation of said breathing gas cooler, wherein said control device controls an amount of water condensation formed in said expiration branch, said breathing gas cooler comprising a Peltier element having a warm side and a cold side, said warm side of said Peltier element being exposed to only said inspired gas flow in said inspiration branch, said cold side being arranged in said expiration branch, said cold side being exposed to only said expired gas flow, wherein said warm side is not in direct fluid communication with said expired gas flow, and said cold side is not in direct fluid communication with said inspired gas flow.

10. A respirator in accordance with claim 9, wherein said control device controls an amount of electricity supplied to said Peltier element such that said control device controls a transfer of heat from said cold side to said warm side, wherein a temperature of said cold side and a temperature of said warm side are controlled by said control device.

11. A respirator in accordance with claim 10, further comprising a water condensation collecting line, said water condensation collecting line receiving said water condensation, wherein said expiration branch has an additional Peltier element with a warm side and a cold side as an additional breathing gas cooler, said cold side of said additional Peltier element being exposed to at least one expired gas flow in said expiration branch.

12. A respirator in accordance with claim 11, wherein said warm side of said additional Peltier element is arranged in a channel, through which cooling air flows.

13. A respirator in accordance with claim 12, further comprising:
a power supply for supplying power to at least one of said Peltier element and said additional Peltier element in a breathing flow-controlled manner.

14. A respirator in accordance with claim 13, wherein one or more of said Peltier element and said additional Peltier element receives control data from said control device.

15. A respirator system comprising:
a respirator with respirator components;
a breathing tube system with an inspiration branch and an expiration branch connected to said respiration components, said inspiration branch receiving an inspired gas flow, said expiration branch receiving an expired gas flow;
a breathing gas cooler module for cooling gas in said expiration branch, said breathing gas cooler module being coupled with said respirator components and being disconnectable therefrom, said breathing gas cooler module comprising a Peltier element having a warm side portion and a cold side portion, said warm side portion being arranged in only said inspiration branch, said warm side portion being exposed to only said inspired gas flow, said cold side portion being arranged in only said expiration branch, said cold side portion being exposed to only said expired gas flow such that heat is removed from said expired gas flow via said cold side portion to form water condensation, wherein said warm side portion is not in direct fluid communication with said expired gas flow, and said cold side portion is not in direct fluid communication with said inspired gas flow; and
a control means for controlling power supplied to said Peltier element such that said control means controls an amount of heat transferred from said cold side portion to said warm side portion, wherein said control means controls an amount of said water condensation formed in said expiration branch.

16. A respirator system in accordance with claim 15, wherein said Peltier element thermally couples said expiration branch with said inspiration branch, said inspired gas flow having a first inspired gas temperature, said warm side portion being in contact with said inspired gas flow, said warm side portion heating said inspired gas flow such that said inspired gas flow has a second inspired gas temperature, said expired gas flow having a first expired gas temperature, said second inspired gas temperature being greater than said first inspired gas temperature, said expired gas flow being cooled via said cold side portion such that said expired gas flow has a second expired gas temperature, said second expired gas temperature being less than said first expired gas temperature.

17. A respirator system in accordance with claim 16, wherein said expiration branch has an additional Peltier element with a warm side and a cold side as an additional breathing gas cooler, said cold side of said additional Peltier element being exposed to at least one expired gas flow in said expiration branch.

18. A respirator system in accordance with claim 16, further comprising:
  a power supply for supplying power to said Peltier element in a breathing flow-controlled manner, wherein said Peltier element receives control data from said control means.

* * * * *